US009558912B2

(12) United States Patent
Kaneko et al.

(10) Patent No.: US 9,558,912 B2
(45) Date of Patent: Jan. 31, 2017

(54) ION MILLING DEVICE (71) Applicant: Hitachi High-Technologies Corporation, Minato-ku, Tokyo (JP)

(72) Inventors: Asako Kaneko, Tokyo (JP); Hisayuki Takasu, Tokyo (JP); Hirobumi Mutou, Tokyo (JP); Toru Iwaya, Tokyo (JP); Mami Konomi, Tokyo (JP)

(73) Assignee: Hitachi High-Technologies Corporation, Tokyo (JP)

(*) Notice: Subject to any disclaimer, the term of this patent is extended or adjusted under 35 U.S.C. 154(b) by 0 days.

(21) Appl. No.: 14/890,936

(22) PCT Filed: Apr. 28, 2014

(86) PCT No.: PCT/JP2014/061809
§ 371 (c)(1),
(2) Date: Nov. 13, 2015

(87) PCT Pub. No.: WO2014/199737
PCT Pub. Date: Dec. 18, 2014

(65) Prior Publication Data
US 2016/0126057 A1    May 5, 2016

(30) Foreign Application Priority Data
Jun. 10, 2013   (JP) ................... 2013-121413

(51) Int. Cl.
*H01J 37/20* (2006.01)
*H01J 37/305* (2006.01)
(Continued)

(52) U.S. Cl.
CPC ............. *H01J 37/20* (2013.01); *G01K 1/14* (2013.01); *H01J 37/3002* (2013.01);
(Continued)

(58) Field of Classification Search
CPC ........... H01J 37/20; H01J 37/3053; G01N 1/32
See application file for complete search history.

(56) References Cited

U.S. PATENT DOCUMENTS

2002/0072112 A1* 6/2002 Atwood ............. B01L 3/50851
435/303.1
2006/0113488 A1* 6/2006 Motoi ..................... G01N 1/32
250/492.21

(Continued)

FOREIGN PATENT DOCUMENTS

JP    11-271192 A    10/1999
JP    2007-248368 A   9/2007

(Continued)

OTHER PUBLICATIONS

International Search Report (PCT/ISA/210) issued in PCT Application No. PCT/JP2014/061809 dated Jun. 17, 2014, with English translation (four (4) pages).

(Continued)

Primary Examiner — Wyatt Stoffa
Assistant Examiner — Eliza Osenbaugh-Stewart
(74) Attorney, Agent, or Firm — Crowell & Moring LLP (57) ABSTRACT

The present invention aims at providing an ion milling apparatus for emitting an ion beam to a sample to process the sample and capable of controlling the temperature of the sample with high accuracy regardless of deformation or the like of the sample being irradiated with the ion beam, and proposes an ion milling apparatus including at least one of a shield holding member for supporting a shield for shielding the sample from the ion beam while exposing a part of the sample to the ion beam; a shifting mechanism for shifting a surface of the sample stand in contact with the sample following deformation of the sample during irradiation with the ion beam, the shifting mechanism having a temperature control mechanism for controlling temperature (Continued)

of at least one of the shield holding member and the sample stand; and a sample holding member disposed between the shield and the sample, the sample holding member deforming following deformation of the sample during irradiation with the ion beam, for example.

13 Claims, 10 Drawing Sheets

(51) Int. Cl.
*H01J 37/302* (2006.01)
*G01K 1/14* (2006.01)
*G01N 1/32* (2006.01)
*H01J 37/30* (2006.01)

(52) U.S. Cl.
CPC ...... *H01J 37/3023* (2013.01); *H01J 37/3053* (2013.01); *G01N 1/32* (2013.01); *H01J 37/30* (2013.01); *H01J 2237/002* (2013.01); *H01J 2237/026* (2013.01); *H01J 2237/08* (2013.01); *H01J 2237/2001* (2013.01); *H01J 2237/2007* (2013.01); *H01J 2237/20271* (2013.01); *H01J 2237/20285* (2013.01); *H01J 2237/317* (2013.01)

(56) References Cited

U.S. PATENT DOCUMENTS

| | | | |
|---|---|---|---|
| 2012/0160471 A1* | 6/2012 | Pfeifer | ............. G01N 1/32 165/287 |
| 2013/0240353 A1* | 9/2013 | Watanabe | ............. H01J 37/20 204/298.36 |

FOREIGN PATENT DOCUMENTS

| | | |
|---|---|---|
| JP | 2008-27602 A | 2/2008 |
| JP | 2008-39667 A | 2/2008 |
| JP | 2009-145050 A | 7/2009 |
| JP | 2009-174940 A | 8/2009 |
| JP | 2010-257856 A | 11/2010 |
| JP | 4922632 B2 | 4/2012 |

OTHER PUBLICATIONS

Japanese-language Written Opinion (PCT/ISA/237) issued in PCT Application No. PCT/JP2014/061809 dated Jun. 17, 2014 (three (3) pages).

* cited by examiner

Examples of micropores of sample holder

ION MILLING DEVICE

TECHNICAL FIELD

The present invention relates to an ion milling apparatus, and in particular relates to an ion milling apparatus including a cooling mechanism.

BACKGROUND ART

Typical example of methods for preparing samples for SEM include freeze fracturing, microtomy, and mechanical polishing, which are suitable for samples having relatively large sizes and being relatively strong. With the freeze fracturing, however, it is difficult to obtain a target observation surface, and it is also difficult to obtain a smooth section. The microtomy is a technique of producing a sample section with a knife, with which it is difficult to obtain a smooth section of a relatively soft sample or the like owing to the stress, and which thus requires proficient skills of operators.

With the mechanical polishing, since a sample section is typically embedded with resin and polished with water or a lubricant, it may be difficult to perform the resin embedding and polishing on a relatively small and soft sample or the like, and it is difficult to perform the mechanical polishing on a sample that should avoid water or the like.

Preparation of a sample section using an ion beam has come into common use recently as a method capable of preparing a sample section with no stress. Ion milling apparatus and method are proposed as means for preparing a sample section by irradiating a sample with an ion beam, in which a shield using a material with a small sputtering yield is disposed on a top surface of the sample in an evacuated sample chamber, a part of about 50 to 200 μm of the sample is exposed from an end surface of the shield and irradiated with an ion beam from the top surface side (on the side of the shield) of the sample, a physical sputtering phenomenon is used to sputter atoms from the sample surface, and a milled surface in a shape along the end surface of the shield is obtained with no stress.

Typically, ion milling conditions of a sample for an electron scanning microscope that are often used are an accelerating voltage of about 10 kV or lower and an ion beam current of about 200 μA or lower. In this case, the quantity of heat applied to the sample by the ion beam irradiation will be about 2 J/s or lower, but since the range of the ion beam irradiation may be a half width of the sample milled surface of about 300 μm and a processing time exceeding several hours, the temperature rise is not negligible in applying ion milling to a sample with a low melting point such as a polymer material.

In order to curb rise in temperature, PTL 1 explains that a braided wire for cooling the shield is connected to the shield. In addition, PTL 2 discloses a section sample preparation method in which a board for radiation is disposed between the shield and the sample so that heat generated by ion beam irradiation is radiated to the sample holder.

CITATION LIST

Patent Literatures

PTL 1: JP 2009-145050 A
PTL 2: JP 2007-248368 A

SUMMARY OF INVENTION

Technical Problem

The heat radiation effect produced by the techniques as described in PTLs 1 and 2 depends on the difference in temperature at a contact between the cooling mechanism and the sample, surface roughness of contact surfaces, and the thermal conductivity of a sample holding structure. Thus, for a sample having such properties as being deformed by heat or vulnerable to heat, heat transfer may be low with the method using the radiation board and the heat radiation effect may be lowered. Furthermore, a sample may be deformed or broken in structure owing to supercooling.

An object of the invention is to provide an ion milling apparatus for emitting an ion beam to a sample for processing the sample, capable of control the temperature of the sample with high accuracy regardless of deformation or the like of the sample while being irradiated with the ion beam.

An ion milling apparatus aimed at achieving sample processing using an ion beam in a proper temperature environment is proposed below.

Solution to Problem

According to an embodiment for achieving the object, proposed is an ion milling apparatus including a sample stand for supporting a sample to be irradiated with an ion beam, the ion milling apparatus including at least one of a shield holding member for supporting a shield for shielding the sample from the ion beam while exposing a part of the sample to the ion beam; a shifting mechanism for shifting a surface of the sample stand in contact with the sample following deformation of the sample during irradiation with the ion beam, the shifting mechanism having a temperature control mechanism for controlling temperature of at least one of the shield holding member and the sample stand; and a sample holding member disposed between the shield and the sample, the sample holding member deforming following deformation of the sample during irradiation with the ion beam.

According to another embodiment for achieving the object, proposed is an ion milling apparatus including a sample stand for supporting a sample to be irradiated with an ion beam, the ion milling apparatus including: a thermometer provided on at least one of a surface of the sample stand in contact with the sample and a surface of a shield in contact with the sample, the shield shielding the sample from the ion beam while exposing a part of the sample to the ion beam; and a temperature control mechanism for controlling temperature of at least one of the sample stand and the shield, wherein the temperature control mechanism controls temperature of at least one of the sample stand and the shield according to a result of temperature measurement of the thermometer.

Advantageous Effects of Invention

According to the features described above, sample processing using an ion beam can be achieved in a proper temperature environment.

DESCRIPTION OF EMBODIMENTS

Embodiments described below mainly relate to an ion milling apparatus and a sample cooling method capable of reliably curbing the rise in the temperature of a sample caused by ion beam irradiation by cooling a shield or the like irradiated with part of an ion beam and in contact with a major part of the sample. When a sample with a low melting point such as a polymer material is to be processed in sample preparation with use of an ion milling apparatus, it is desirable to consider the influence of heat on the sample due to ion beam irradiation and the influence of shrinkage of the sample due to supercooling of the sample. If a sample shrinks, for example, the contact between a shield or the like that is a temperature transfer medium of a cooling mechanism and the sample becomes insufficient, which decreases the cooling efficiency.

The embodiments described below will, firstly, propose an ion milling apparatus provided with a shield cooling mechanism using liquid nitrogen or the like so as to curb the rise in the temperature of a sample caused by an ion beam and thus reduce thermal damage on the sample.

Furthermore, the embodiments will propose, in use of the ion milling apparatus, sample preprocessing of providing a material having a good thermal conductivity (such as metal, ionic liquid, or paste, for example) between the shield and the shield to efficiently radiate heat at a processed surface of the sample to the shields so as to reduce softening of the sample due to thermal damage or the like.

Secondly, the embodiments will propose provision of sample and sample stand holding mechanisms in which an elastic member such as a spring is used for a sample stand itself of the ion milling apparatus to make a sample into contact with the shield, so that the sample and the shield can be sufficiently in contact with each other and the sample can be cooled even when the sample shrinks during cooling. The embodiments will also propose provision of a shield holder that is elastic and allows a sample and the shield to be sufficiently in contact with each other for cooling even when the sample shrinks during cooling, and a sample holder that is disposed between the sample and the shield, has micropores to which ionic liquid is applied, and is capable of increasing thermal conductivity, the sample holder being capable of efficiently transfer heat accumulated in the sample by an ion beam to the shield.

The embodiments will further propose an ion milling apparatus further provided with heaters for heating the shield and the sample and controllers of the heaters, and a temperature sensor for the shield and a controller of the temperature sensor, so that a surface to be processed of the sample is processed with the temperature kept at a set temperature.

According to the configurations as described above, a sufficient contact between a sample and a shield on a cooling side can be maintained during processing and cooling of the sample, and heat accumulated in the sample by an ion beam is efficiently transferred to the shield, which reduces thermal damage caused by the ion beam on the sample.

Hereinafter, a specific configuration of an ion milling apparatus will be described with reference to the drawings.

First Embodiment

Figure 1:
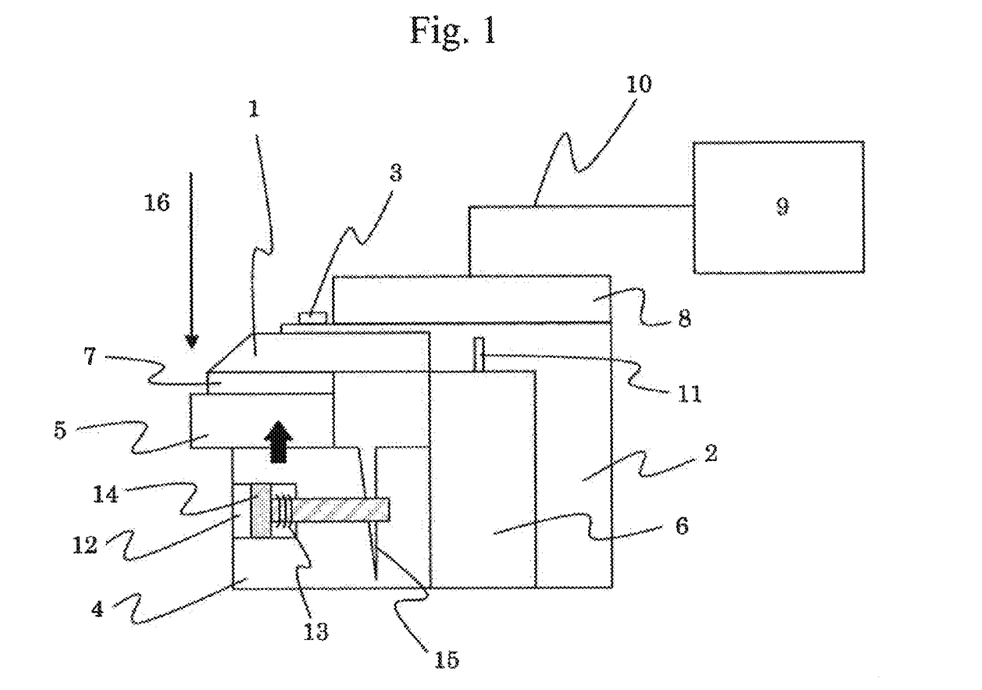
FIG. 1 is a diagram illustrating an embodiment of an ion milling apparatus including a mechanism for increasing adhesion between a shield and a sample and a cooling mechanism for cooling the shield.

FIG. 1 is a diagram illustrating an embodiment of an ion milling apparatus. In an ion milling apparatus according to the present invention, a shield 1 is fixed to a shield holding part 2 with a shield fixing screw 3, a sample 5 fixed the sample stand 4 is fixed to a sample stand holding part 6 together with the sample stand 4, and a top surface of the sample 5 is in close contact with a bottom surface of the shield 1 with a sample holder 7 therebetween. The shield 1 serves to shield the sample 5 from an ion beam 16 while exposing a part of the sample 5 to the ion beam 16.

The shield 1 is in contact with a shield cooling plate 8, and liquid nitrogen 9 cools the shield 1, the sample holder 7, and sample 5 via a braided wire 10. A cooling mechanism (temperature control mechanism) presented in the present embodiment is configured to cool at least one of the sample stand 4 and the shield holding part 2 (shield holding member). The sample holder 7 (sample holding member) is elastic, and the adhesion between the top surface of the sample 5 and the bottom surface of the shield 1 can always be maintained with the sample holder 7 even when the sample 5 changes in volume as a result of cooling. Even when the sample 5 undergoes shrinkage deformation as a result of cooling or undergoes expansion deformation as a result of irradiation with the ion beam 16, for example, the surface of the sample holder 7 in contact with the sample 5 moves following the deformation, which can maintain high adhesion.

The sample holder has micropores, and a material 20 having a good thermal conductivity such as ionic liquid is applied thereto, causing surface tension that can increase the adhesion between the top surface of the sample 5 and the bottom surface of the shield 1. The shield holding part 2 has a shield holding part groove 11 formed therein, which functions elastically. When the sample 5 fixed to the sample stand 4 is pressed up and brought into contact with the shield 1, the elasticity of the shield holding part groove 11 can increase the adhesion between the shield 1 and the sample 5. The groove 11 is to deform the shield holding part 2 with a shift in position of the shield 1, and deforms the shield holding part 2 with a bottom of the groove 11 or the vicinity thereof being a support point therefor.

Furthermore, the sample stand 4 has a slot 12 in which a fixing screw 14 is disposed therein with a spring 15. The sample stand 4 has a sample stand groove 15 formed therein, and the fixing screw 14 is disposed so as to be fixed across the sample stand groove 15. As the fixing screw 14 is tightened, the sample stand 4 can be lifted in the direction of the arrow in FIG. 1, which is expected to produce the effect of increasing the adhesion between the shield 1 and the sample 5. As a result of increasing the adhesion between the shield 1 and the sample 5 in this manner, the heat of the sample 5 accumulated in the shield 1 on the cooling side by the ion beam 16 can be efficiently radiated even when the volume of the sample 5 changes as a result of cooling. The spring 13 acts in such a manner as to move the surface of the sample stand 4 in contact with the sample (presses the sample) following the deformation of the sample, which can maintain, high adhesion between the sample stand 4 and the sample 5 regardless of the deformation of the sample 5.

Figure 2:
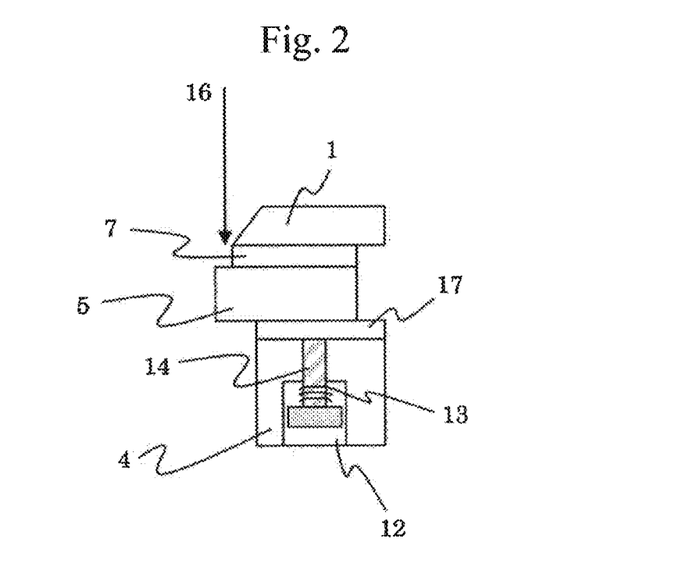
FIG. 2 is a diagram illustrating another embodiment of a sample stand including a mechanism for increasing the adhesion between the shield and the sample.

FIG. 2 is a diagram illustrating another example of the sample stand 4 illustrated in FIG. 1. The sample stand 4 is in contact with the shield 1 with the sample holder therebetween. A sample stand push plate 17 is disposed between the sample stand 4 for fixing the sample 5 and the sample 5, the slot 12 is formed in a bottom surface of the sample stand 4, and the fixing screw 14 is disposed therein with the spring 13. As the fixing screw 14 is tightened, the sample stand push plate 17 is lifted toward the shield 1 owing to the elasticity of the spring 13, and the adhesion between the top surface of the sample 5 and the bottom surface of the shield 1 with the sample holder 7 therebetween can be increased. As a result of increasing the adhesion between the shield 1 and the sample 5 in this manner, the heat of the sample 5 accumulated in the shield 1 on the cooling side by the ion beam 16 can be efficiently radiated even when the volume of the of the sample 5 changes as a result of cooling.

Figure 3:
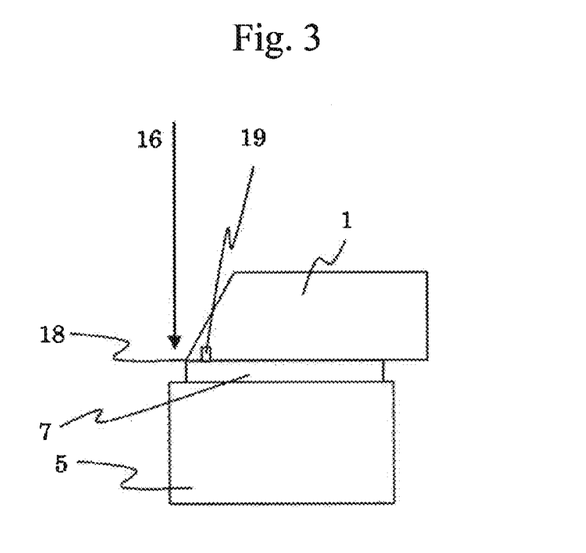
FIG. 3 is a diagram illustrating an embodiment of a position and a manner of holding of the sample holder.

FIG. 3 is a detail view of the shield 1 when the sample holder 7 illustrated in FIG. 1 or 2 is used. The sample holder 7 is disposed between the sample 5 and the shield 1. In order to shorten the processing time of the sample 5, prevent redeposition (a phenomenon that particles resulting from sputtering the surface of the sample 5 with the ion beam 16 are redeposited on the processed surface of the sample 5, and avoid problems such as carbonization of ionic liquid filled in the sample holder 7 due to the heat of the ion beam 16, it is suitable to make the sample holder 7 flush with a shield end portion 18.

A shield groove 19 is formed near the shield end portion 18, and the micropores formed in the sample holder 7 and the ionic liquid with which the micropores is filled enter the shield groove 19 when being brought into contact with the shield 1 and the sample holder 7. As a result, the surface tension of the ionic liquid causes the shield 1 and the sample holder 7 to be fixed to each other in such a manner that the sample holder 7 does not protrude from the shield end portion 18 to the front surface that is a processed surface.

Figure 12:
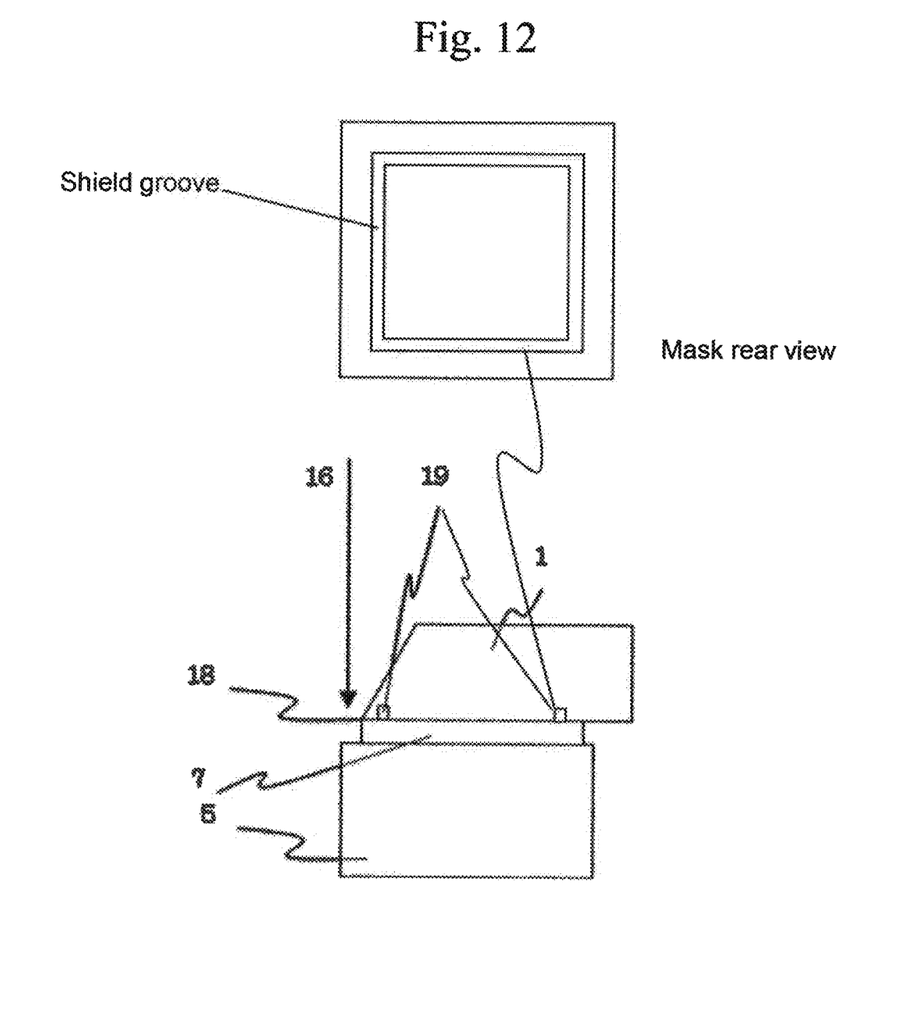
FIG. 12 is a diagram illustrating an embodiment of a position and a manner of holding of a sample holder.

Alternatively, the shield groove 19 illustrated in FIG. 3 may be formed through the entire end portion of a mask as illustrated in FIG. 12 instead of being formed only near the shield end portion 18. As a result of forming the shield groove through the entire end portion of the mask (forming grooves corresponding to the respective sides of a square mask), the adhesion between the shield 1 and the sample holder 7 can further be increased, and the effect of prevent tog permeation or leakage of the ionic liquid with which the sample holder 7 is filled into the processing surface of the sample and surrounding components is produced.

Figure 4:
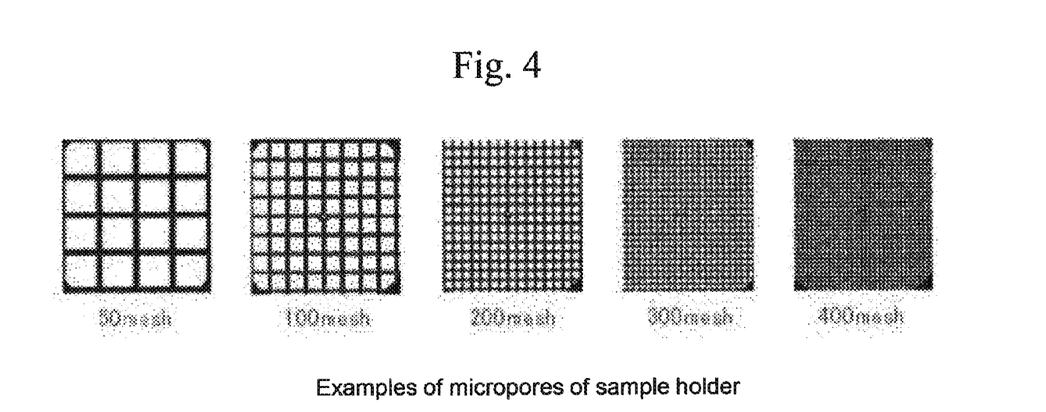
FIG. 4 illustrates examples of the sample holder having micropores.

FIG. 4 is an example of illustration of exemplary micropores of the sample holder 7. It is suitable to use a material (porous member) having micropores such as a microgrid mesh used in observation with a transmission electron microscope or the like. As a result of filling the micropores with ionic liquid that does not evaporate in vacuum, the adhesion between the shield 1 that is a medium transferring the temperature from the cooling mechanism and the sample 5 can be kept high.

The microgrid meshes illustrated in FIG. 4 are subjected to etching such as plasma etching on the surfaces thereof so that the wettability of the mesh surfaces are improved, and further have ionic liquid with low surface tension used therein, which makes the ionic liquid easily enter the fine meshes and can thus be expected to further improve the adhesion between the shield. 1 and the sample holder 7.

Figure 5:
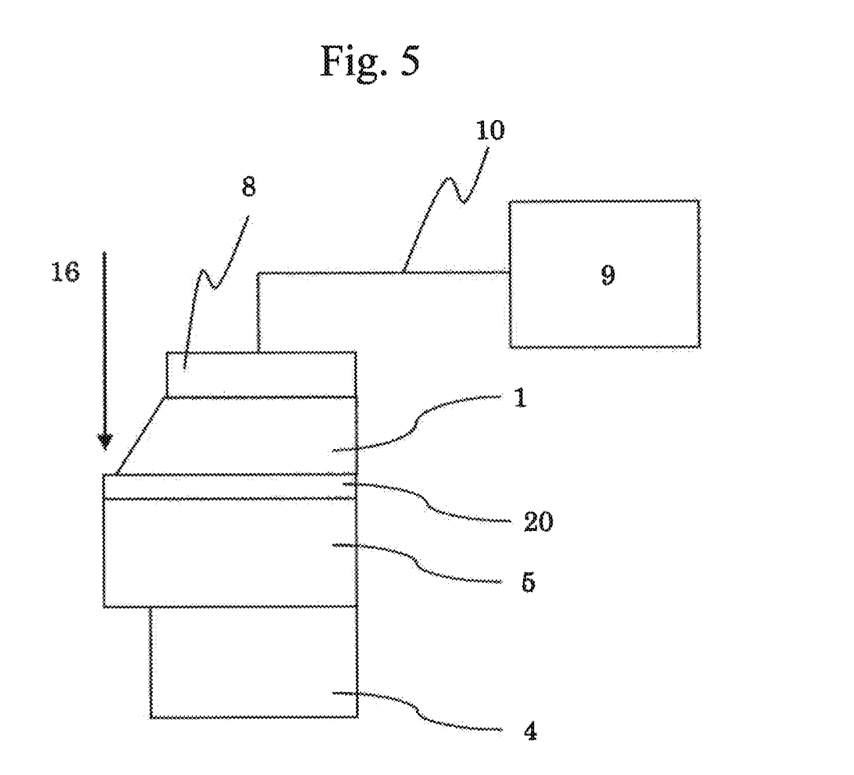
FIG. 5 is a diagram illustrating an example in which a highly thermally conductive member is disposed between the shield and the sample.

FIG. 5 is a diagram illustrating an example in which the sample 5 and a highly thermally conductive material 20 are disposed on the surface of the sample stand 4 in contact, with the sample 5. As a result of providing the highly thermally conductive material 20 between the sample 5 and the shield 1, the heat of the sample 5 raised in temperature by the ion beam 16 can be radiated to the shield 1. Note that the highly thermally conductive material 20 provided between the sample 5 and the shield 1 is suitably a metallic material (such as a metal sheet, a metal foil, or metal powder, for example), ionic liquid that can be kept in a liquid state in vacuum, or a paste material such as carbon paste or silver paste. Furthermore, as a result of providing the highly thermally conductive material 20 between the sample 5 and the shield 1, the efficiency of holding the sample 5 or protecting the sample 5 can also be achieved. Furthermore, in such a case where the top surface of the sample 5 which is in direct contact with the shield 1 is an irregular surface, in particular, ionic liquid, carbon paste, or silver paste is applied on the top surface of the sample 5 to compensate for the irregularity of the top surface so as to increase the adhesion to the shield 1, which can also produce the effect of reducing processing defects such as streaks caused by processing. Note that, when ionic liquid is used, a good processed surface can be obtained by using the ionic liquid only on the portion shielded by the shield 1 so that the ionic liquid applied to a region irradiated directly with the ion beam 16 will be minimized so as to be prevented from being carbonized by the heat of the ion beam 16.

Figure 6:
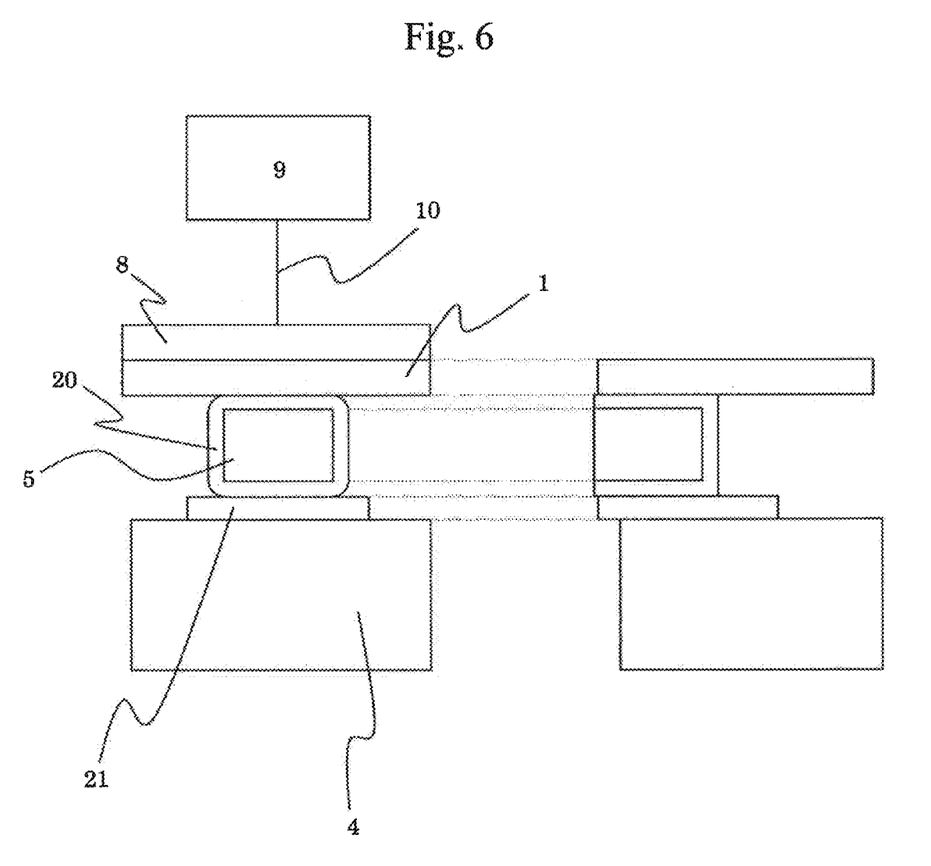
FIG. 6 is a diagram illustrating an example in which a sample to be processed is covered with a highly thermally conductive member.

FIG. 6 is a diagram illustrating an example in which the sample 5 coated with a highly thermally conductive member is subjected to ion milling. Hereinafter, a sample preprocessing method effective, in particular, for a sample with poor thermal conductivity or a sample having a relatively large thickness will be described.

The entire sample 5 except for the surface to be processed of the sample 5 is covered with the highly thermally conductive material 20, and the sample 5 is fixed onto a relatively strong member such as a plate 21 with an adhesive or a paste of fixing material so that the sample 5 is held. Note that the highly thermally conductive material 20 covering the entire sample 5 is suitably a metallic material (such as a metal sheet, a metal foil, or metal powder, for example), ionic liquid that can be kept in a liquid state in vacuum, or a pate material such as carbon paste or silver paste, similarly to FIG. 5. The effect of efficiently radiating heat from the entire sample 5 to the shield 1 can thus be expected.

Figure 7:
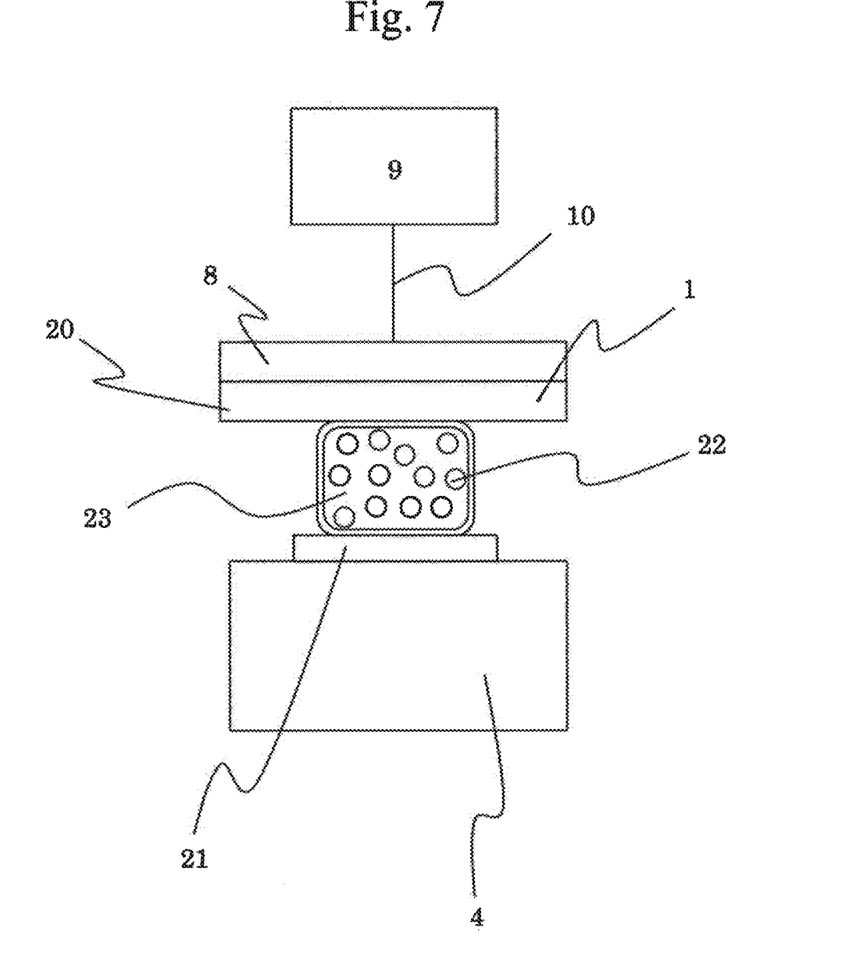
FIG. 7 is a diagram illustrating an example in which a powder sample is fixed with a paste member and processed.

FIG. 7 is a diagram illustrating an example in which a minute sample is subjected to ion milling. In this example, an example in which the minute sample is a powder sample 22 will be described. The powder sample 22 is mixed with a resin or paste material 23, and coated with highly thermally conductive material 20, and the sample 5 is fixed onto a relatively strong member such as a plate 21 with an adhesive or a paste of fixing material so that the sample 5 is held. Note that the highly thermally conductive material 20 coating the entire sample 5 is suitably a metallic material (such as a metal sheet or a metal foil, for example). The effect of efficiently radiating heat from the entire sample 5 to the shield 1 can thus be expected. Furthermore, as a result of coating the entire sample 5, the effect of fixing or holding the sample 5 can also be expected.

Second Embodiment

Figure 8:
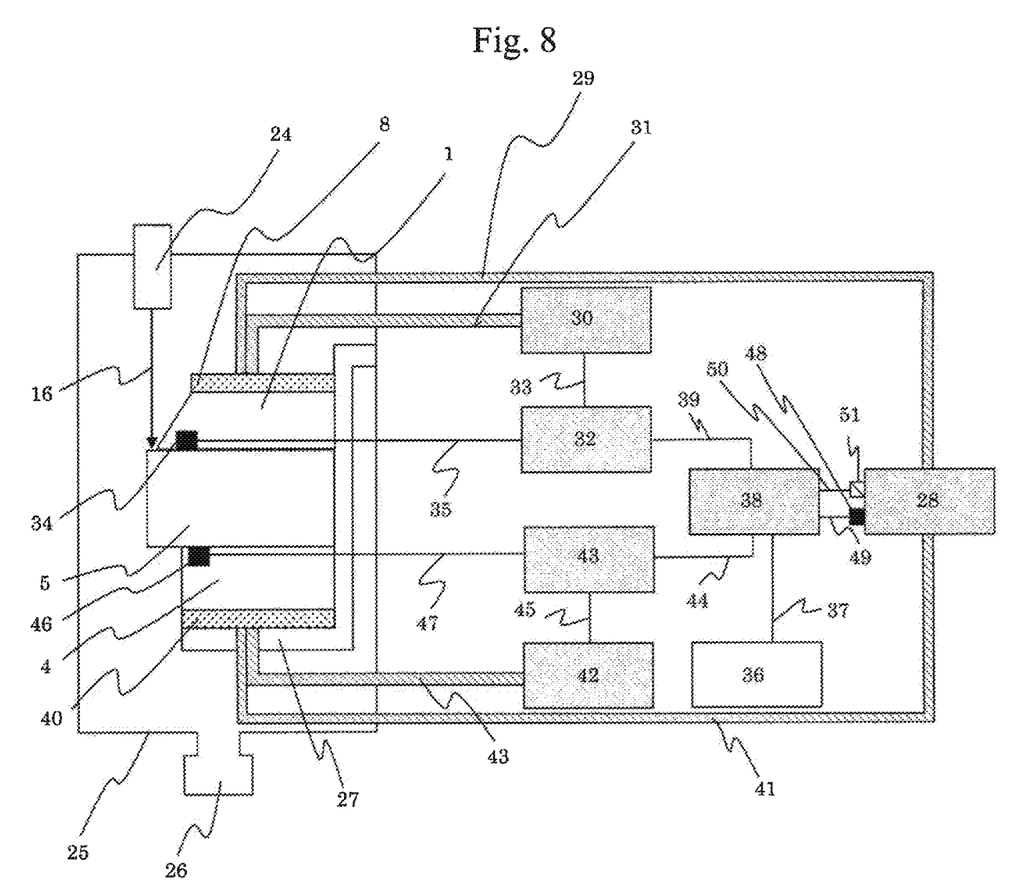
FIG. 8 is a diagram illustrating an ion milling apparatus including a temperature controller.

FIG. 8 is a diagram illustrating an embodiment of an ion milling apparatus with a shield 1 and a sample stand cooling mechanism capable of controlling the sample temperature. The ion milling apparatus according to the present embodiment includes an ion source 24, a sample chamber 25, a vacuum pump 26, and a sample stage 27.

The ion milling apparatus is a sample preprocessing apparatus configured to generate ions with the ion source 24, emit an ion beam 16 to a sample 5 from the ion source 24 to sputter atoms from a sample surface so as to smooth the sample 5 with no stress. The ion milling apparatus is primarily used as an apparatus for preprocessing a sample to be observed with an electron microscope.

The ion milling apparatus illustrated in FIG. 8 is provided with a shield cooling plate 8 on the shield 1 disposed on the top of the sample 5 in addition to a sample stand 4 and the sample 5 set on the sample stage 27. The shield cooling plate 8 and a liquid nitrogen dewar 28 are connected by a braided wire 29 (a mesh electrode wire, which is a mesh wire or the like formed into a wire, for example), and the shield 1 can be cooled directly by liquid nitrogen 9 poured into the liquid nitrogen dewar 28 through the braided wire 29.

The shield cooling plate 8 is also connected to a heater 30 via a braided wire 31. The heater 30 is connected to a controller 32 by a wire 33. The heater 30 can heat the shield 1 via the braided wire 31. The shield 1 is provided with a temperature sensor 34 (thermometer), which is connected to the controller 32 via a wire 35.

A signal (temperature information of the shield) detected by the temperature sensor 34 is sent to the controller 32 via the wire 35. The user can freely set a temperature at a sample processing part in advance by using an operation panel 36 (temperature set by the user (=desired sample processed surface temperature)), and the set information is sent to the controller 32 via a wire 37 a main controller 38, and a wire 39. The controller 32 compares a measured temperature measured by temperature sensor 34 (measured temperature+calibration value (calibration value (details of which will be explained with reference to FIG. 9))) with the temperature set by the user, and determines whether or not to control the heater. If the heater is to be controlled, a signal for operational instruction is sent to the heater 30 via the wire 33.

In the ion milling apparatus illustrated in FIG. 8, the sample stand 4 for fixing the sample 5 is also provided with a function similar to that of the cooling mechanism of the shield in addition to the mechanism for directly cooling the shield 1. A sample stand cooling plate 40 in direct contact with the sample stand 4 is provided on a bottom surface of the sample stand 4. The sample stand cooling plate 40 and the liquid nitrogen dewar 28 are connected by a braided wire 41. The sample stand 4 can be cooled by liquid nitrogen 9 poured into the liquid nitrogen dewar 28 via the braided wire 41 similarly to the cooling of the shield 1.

The sample stand cooling plate 40 is connected to a heater 42 via a braided wire 43. The heater 42 is connected with a controller 43 by a wire 44. The heater 42 can heat the sample stand 4 via the braided wire 43. The sample stand 4 is provided with a temperature sensor 46, which is connected to the controller 43 via a wire 47.

A signal (temperature information of the sample stand) detected by the temperature sensor 45 is sent to the controller 43 via the wire 47. Similarly to the temperature control of the shield, temperature information set by the user that has been input by the user using the operation panel 36 is sent to the controller 43 via the wire 37, the main controller 38, and the wire 44. The controller 43 compares a measured temperature measured by the temperature sensor 46 (measured temperature+calibration value (calibration value (details of which will be explained, with reference to FIG. 9))) with the temperature set by the user, and determines whether or not to control the heater. If the heater is to be controlled, a signal for operational instruction is sent to the heater 42 via a wire 45.

The ion milling apparatus illustrated in FIG. 8 includes a thermometer on at least one of a surface of the sample stand in contact with the sample and a surface of the shield in contact with the sample, the shield shielding the sample from an ion beam while exposing a part of the sample to the ion beam, in which the temperature control mechanism (controller) for controlling the temperature of at least one of the sample stand and the shield is configured to control the temperature of at least one of the sample stand and the shield according to a temperature measurement result of the thermometer. Hereinafter, specific examples of temperature control performed by the temperature control mechanism (the controller 32, the controller 43) will be described in detail with reference to FIGS. 9 and 10.

Note that the liquid nitrogen dewar 28 is provided with a fluid level sensor 48. When the liquid nitrogen 9 poured into the liquid nitrogen dewar 28 becomes lower than a predetermined fluid level, the fluid level sensor sends a signal indicating this state to the main controller 38 via a wire 49. The main controller 38 is configured to turn on an LED 51 via a wire 50, and the user can thus know the timing when to replenish the liquid nitrogen.

Since the shield 1 and the sample stand 4 are directly cooled by the liquid nitrogen 9, the effect of shortening the time for cooling the sample 5 as compared to the case where only one of the shield 1 and the sample stand 4 is cooled can be expected. Similarly, since the shield 1 and the sample stand are both provided with temperature control mechanisms separate from each other and provided with mechanisms that individually heat the shield 1 and the sample stand 4, respectively, with heaters, temperature control can be performed more efficiently and in a shorter time than the case where temperature control of the sample 5 is performed with the heater of either one of the shield 1 and the sample stand 4, particularly after finishing sample processing until returning the sample temperature to normal temperature.

Figure 9:
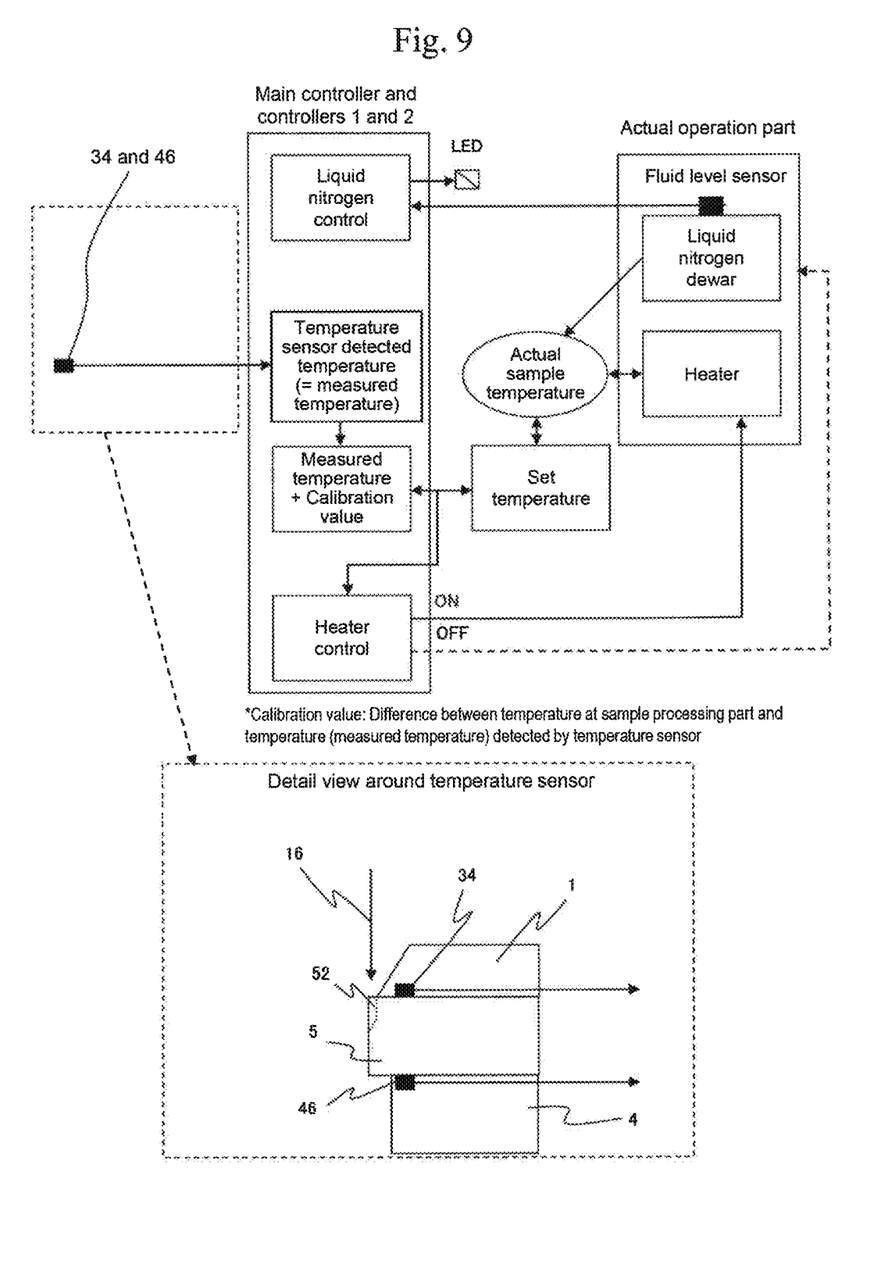
FIG. 9 is a diagram illustrating a control system of an ion milling apparatus including a temperature controller.

FIG. 9 is a schematic diagram of details of the temperature control illustrated in FIG. 8 and overall control of peripheral mechanisms. As illustrated in a detail view of around a temperature sensor, if the temperature sensor 34 is sputtered by the ion beam 16, the temperature sensor 34 may not output correct temperature information or redeposition, streaks caused by processing, or the like may occur, and it is thus difficult to install the temperature sensor 34 directly at a processing region of the sample 5 that is at the center of the ion beam 16.

In the present embodiment, an example in which the temperature sensor 34 is mounted above the sample 5 and on the bottom surface of the shield 1 at a position shifted toward the shield 1 from the center of the ion beam 16 will therefore be described, which results in a difference between the temperature (measured temperature) detected at the position of the temperature sensor 34 and the temperature at the processed surface of the sample. This temperature difference varies depending on sample processing conditions such as the material of the sample 5 and the ion beam 16 (such as accelerating voltage/ion beam current) emitted to the sample 5. Thus, the temperature difference in a case where processing is performed under the processing conditions is held as a calibration value in the controller, and added to the temperature (measured temperature) detected by the temperature sensor 134 to obtain the temperature of the sample processed surface.

Similarly for the temperature sensor 46, in order to avoid adverse effects on the operation of the temperature sensor 46 itself caused by the ion beam 16 and direct adverse effects of the temperature sensor 46 on the sample processed surface, the temperature sensor 46 is positioned below the sample 5 and on the top surface of the sample stand 4 at a position shifted toward the sample stand 4 from the center of the ion beam 16, which results in a difference between the temperature (measured temperature) detected at the position of the temperature sensor 46 and the temperature at the sample processed surface. Thus, a calibration value is set in advance similarly to the temperature sensor 34.

Since the calibration value varies depending on the type of the sample and processing conditions (accelerating voltage, beam current, etc.) calibration values for respective combinations of the sample type and the processing conditions may be stored in advance in a not-illustrated storage medium, for example, a calibration value may be read therefrom on the basis of a selection of the sample type and the processing conditions, and a value obtained by adding the calibration value may be an output of a thermometer. Alternatively, an arithmetic operation using the processing conditions and the like as parameters may be stored in a storage medium, a calibration value may be calculated on the basis of a selection of the processing conditions (selection of parameters), and a value obtained by adding the calibration value may be an output of a thermometer.

The controller 32 or the controller 43 compares a measured temperature+the calibration value, the measured temperature being measured by the temperature sensor 34 or the temperature sensor 246, with a certain set temperature (the temperature set by the user) set by the user in advance with use of the operation panel 36, and determines whether to turn on/off the heater. (Details of determination on control on turning on/off the heater will be described with reference to FIG. 10.) if the heater is to be turned on, the sample 5 is heated by the heater under the heater control. If the heater is to be turned off, the sample 5 is cooled by the liquid nitrogen 9. Note that cooling of the sample 5 by the liquid nitrogen 9 is always on whether the heater is turned on or off. Furthermore, when the fluid level sensor 48 is provided in the liquid nitrogen dewar 28 and if the liquid nitrogen 9 poured into the liquid nitrogen dewar 28 becomes lower than a predetermined fluid level, the fluid level sensor 48 operates to send a signal to the controller, which in turn sends an LED 51 lighting signal to turn on the LED 51, so that the user is informed of a sign for replenishing the liquid nitrogen 9.

Figure 10:
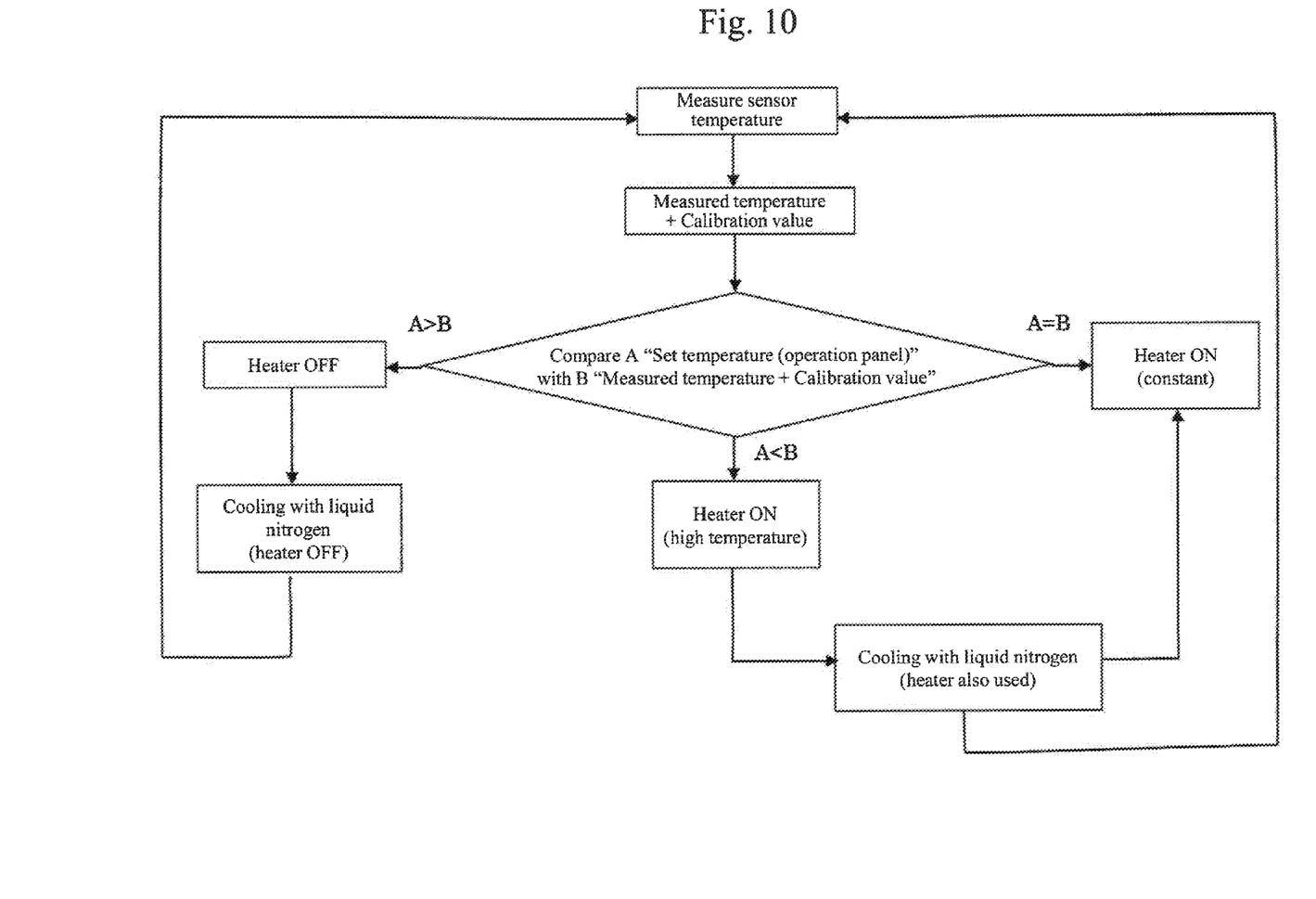
FIG. 10 is a flowchart illustrating a temperature control process.

FIG. 10 illustrates details of the heater control performed by the main controller and the controllers 1 and 2 illustrated in FIG. 9 in a form of a flowchart. The temperature sensors measure the temperatures of the shield 1 and the sample stand 4, and add the calibration values to the measured temperatures (the temperatures of the shield and the sample stand). The measured temperatures+the calibration values are compared with the set temperatures set by the user with use of the operation panel. If a "measured temperature+calibration value=temperature set by the user," the heater is turned on to keep the heater temperature constant, and the temperature of the shield 1 or the sample stand 4 is controlled together with the cooling with the liquids nitrogen. If "measured temperature+calibration value<temperature set by the user," the heater is turned on with the heater temperature set to a high temperature, and the temperature of the shield 1 or the sample stand 4 is controlled together with the cooling with the liquid nitrogen. If "measured temperature+calibration value>temperature set by the user," the heater is turned off and the temperature of the shield 1 or the sample stand 4 is controlled by cooling with the liquid nitrogen. The control in the flowchart illustrated in FIG. 10 is always repeated so that "measured temperature+calibration value=temperature set by the user" is obtained.

Figure 11:
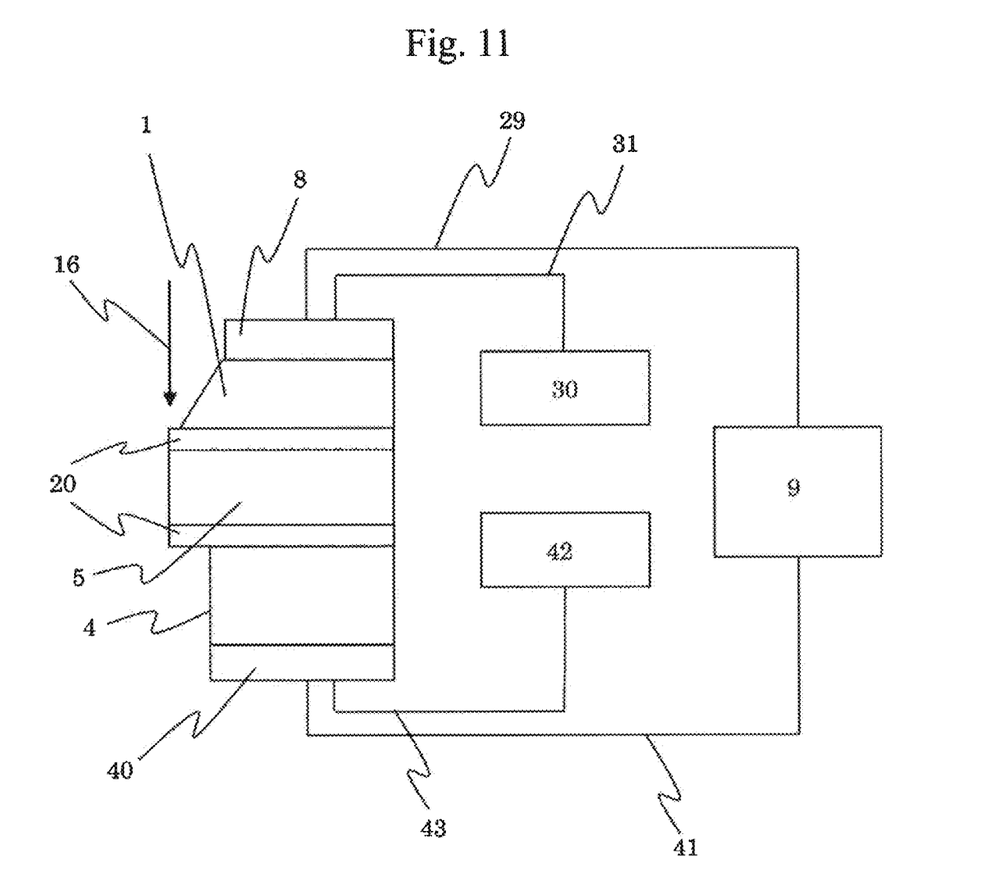
FIG. 11 is a diagram illustrating an ion milling apparatus including a temperature controller.

FIG. 11 is a diagram illustrating an example of an ion milling apparatus including a temperature control mechanism. The ion milling apparatus illustrated in FIG. 11 includes a shield cooling plate 8 provided on the top of the shield 1, means for cooling a sample 5 with liquid nitrogen 9 via a braided wire 29, means for cooling the sample 5 with liquid nitrogen 9 via a sample stand cooling plate 40 provided on the bottom surface of the sample stand 4 and a braided wire 41, means for controlling the temperature of the sample 5 with a heater 30 via the shield cooling plate 8 and a braided wire 31, and means for controlling the temperature of the sample 5 with a heater 42 via the sample stand cooling plate 40 and a braided wire 43.

In the example illustrated in FIG. 11, highly thermally conductive materials 20 are disposed on the top surface and the bottom surface of the sample 5 in such a manner as to be in direct contact with the shield 1 and the sample stand 4. As a result of preprocessing the sample so that the highly thermally conductive materials 20 are disposed, the effect of facilitating cooling of the sample 5 with liquid nitrogen 9 and temperature control of the sample 5 with the heaters can be expected. Furthermore, the highly thermally conductive materials 20 may be sample holders 7 having micropores and elasticity as illustrated in FIG. 4, and the micropores of the sample holders 7 may be filled with the highly thermally conductive materials 20 such as ionic liquid. As a result of filling the micropores with ionic liquid, the adhesion between the sample 5 and the shield 1 and the adhesion between the sample 5 and the sample stand 4 can be increased, which can increase the cooling efficiency and the temperature control efficiency as a result. Furthermore, the ion milling apparatus and the sample preprocessing methods illustrated in FIGS. 6 an 7 can be combined, with which the effect of cooling and temperature control of the top and bottom surfaces of the sample 5 can be expected.

REFERENCE SIGNS LIST 2 shield holding part
3 shield fixing screw
4 sample stand
5 sample
6 sample stand holding part
7 sample holder
8 shield cooling plate
9 liquid nitrogen
10 braided wire
11 shield holding part groove
12 slot
13 spring 14 fixing screw
15 sample stand groove
16 ion beam
17 sample stand push plate
18 shield end portion
19 shield groove
20 highly thermally conductive material
21 plate
22 powder sample
23 resin or paste material
24 ion source
25 sample chamber
26 vacuum pump
27 sample stage
28 liquid nitrogen dewar
29 braided wire 1
30 heater 1
31 braided wire 2
32 controller 1
33 wire 5
34 temperature sensor 1
35 wire 1
36 operation panel
37 wire 7
38 main controller
39 wire 3
40 sample stand cooling plate
41 braided wire 4
42 heater 2
43 braided wire 3
44 wire 4
45 wire 6
46 temperature sensor 2
47 wire 2
48 fluid level sensor
49 wire 9
50 wire 8
51 LED
52 processing part

The invention claimed is:

1. An ion milling apparatus including a sample stand for supporting a sample to be irradiated with an ion beam, the ion milling apparatus comprising at least one of:
a shield holding member for supporting a shield for shielding the sample from the ion beam while exposing a part of the sample to the ion beam; a shifting mechanism for shifting a surface of the sample stand in contact with the sample following deformation of the sample during irradiation with the ion beam, the shifting mechanism having a temperature control mechanism for controlling temperature of at least one of the shield holding member and the sample stand; and a sample holding member disposed between the shield and the sample, the sample holding member deforming following deformation of the sample during irradiation with the ion beam.

2. The ion milling apparatus according to claim 1, wherein the shifting mechanism includes a pressing member for pressing the sample toward the shield.

3. The ion milling apparatus according to claim 2, wherein the pressing member includes an elastic member for pressing the sample.

4. The ion milling apparatus according to claim 3, wherein the elastic member is a spring.

5. The ion milling apparatus according to claim 2, wherein the shield holding member has a groove therein for deforming the shield holding member when being pressed by the pressing member.

6. The ion milling apparatus according to claim 1, wherein the sample holding member is a porous member.

7. The ion milling apparatus according to claim 6, wherein pores of the sample holding member are filled with liquid that transfers heat.

8. The ion milling apparatus according to claim 1, wherein the temperature control mechanism is a cooling mechanism for cooling the sample.

9. An ion milling apparatus including a sample stand for supporting a sample to be irradiated with an ion beam, the ion milling apparatus comprising:
a thermometer provided on at least one of a surface of the sample stand in contact with the sample and a surface of a shield in contact with the sample, the shield shielding the sample from the ion beam while exposing a part of the sample to the ion beam; a sample holding member disposed between the shield and the sample, the sample holding member moving with the sample as the sample undergoes volume change; and a temperature control mechanism for controlling temperature of at least one of the sample stand and the shield, wherein
the temperature control mechanism controls temperature of at least one of the sample stand and the shield according to a result of temperature measurement of the thermometer.

10. The ion milling apparatus according to claim 9, wherein the thermometer is in contact with the sample and disposed at a position out of a region irradiated with the ion beam.

11. The ion milling apparatus according to claim 10, wherein the temperature control mechanism calibrates a temperature measured by the thermometer and controls the temperature on a basis of the calibrated temperature.

12. The ion milling apparatus according to claim 9, wherein the temperature control mechanism includes a first thermometer disposed on a side of a surface of the sample irradiated with the ion beam, a second thermometer disposed on a side of a surface opposite to the surface irradiated with the ion beam, a first temperature control mechanism for controlling temperature of the surface of the sample irradiated with the ion beam on a basis of a measurement result obtained by the first thermometer, and a second temperature control mechanism for controlling temperature of the surface opposite to the surface irradiated with the ion beam on a basis of a measurement result obtained by the second thermometer.

13. The ion milling apparatus according to claim 9, wherein the temperature control mechanism includes a heating mechanism for heating the sample and a cooling mechanism for cooling the sample.

* * * * *